(12) United States Patent
Ford

(10) Patent No.: US 9,193,811 B2
(45) Date of Patent: *Nov. 24, 2015

(54) EXPANDABLE TFE COPOLYMERS, METHOD OF MAKING, AND POROUS, EXPANDED ARTICLES THEREOF

(71) Applicant: W. L. Gore & Associates, Inc., Newark, DE (US)

(72) Inventor: Lawrence A. Ford, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 72 days.

This patent is subject to a terminal disclaimer.

(21) Appl. No.: 14/096,089

(22) Filed: Dec. 4, 2013

(65) Prior Publication Data

US 2014/0094557 A1 Apr. 3, 2014

Related U.S. Application Data

(63) Continuation of application No. 12/408,153, filed on Mar. 20, 2009, which is a continuation-in-part of application No. 11/906,877, filed on Oct. 4, 2007, now Pat. No. 8,637,144.

(51) Int. Cl.

| | |
|---|---|
| *C08F 259/08* | (2006.01) |
| *C08F 14/26* | (2006.01) |
| *A61L 27/16* | (2006.01) |
| *A61L 27/50* | (2006.01) |
| *A61L 27/56* | (2006.01) |
| *A61L 31/04* | (2006.01) |
| *A61L 31/14* | (2006.01) |
| *B29C 55/00* | (2006.01) |
| *C08F 214/26* | (2006.01) |
| *C08J 9/00* | (2006.01) |
| *B29K 27/18* | (2006.01) |
| *B29K 105/04* | (2006.01) |

(52) U.S. Cl.
CPC ............... *C08F 14/26* (2013.01); *A61L 27/16* (2013.01); *A61L 27/507* (2013.01); *A61L 27/56* (2013.01); *A61L 31/048* (2013.01); *A61L 31/146* (2013.01); *B29C 55/005* (2013.01); *C08F 214/26* (2013.01); *C08F 214/262* (2013.01); *C08F 214/265* (2013.01); *C08F 259/08* (2013.01); *C08J 9/00* (2013.01); *B29K 2027/18* (2013.01); *B29K 2105/04* (2013.01); *C08J 2207/02* (2013.01); *C08J 2327/18* (2013.01); *Y10T 428/1376* (2015.01)

(58) Field of Classification Search
CPC .................................................. C08F 259/08
See application file for complete search history.

(56) References Cited

U.S. PATENT DOCUMENTS

| | | |
|---|---|---|
| 3,196,194 A | 7/1965 | Ely, Jr. et al. |
| 3,655,611 A | 4/1972 | Mueller |
| 3,929,950 A | 12/1975 | Nakamura et al. |
| 3,953,566 A | 4/1976 | Gore |
| 4,016,345 A | 4/1977 | Holmes |
| 4,036,802 A | 7/1977 | Poirer |
| 4,038,231 A | 7/1977 | Downer |
| 4,129,618 A | 12/1978 | Downer |
| 4,187,390 A | 2/1980 | Gore |
| 4,194,041 A | 3/1980 | Gore |
| 4,381,384 A | 4/1983 | Khan |
| 4,391,940 A | 7/1983 | Kuhls |
| 4,469,744 A | 9/1984 | Grot |
| 4,518,650 A | 5/1985 | Grot |
| RE31,907 E | 6/1985 | Poirer |
| 4,576,869 A | 3/1986 | Malhotra |
| 4,623,670 A | 11/1986 | Mutoh et al. |
| 4,675,380 A | 6/1987 | Buckmaster |
| 4,742,122 A | 5/1988 | Buckmaster |
| 4,770,927 A | 9/1988 | Effenberger |
| 4,780,490 A | 10/1988 | Mizuno et al. |
| 4,792,594 A | 12/1988 | Gangal |
| 4,824,511 A | 4/1989 | Hartman et al. |
| 4,830,062 A | 5/1989 | Yamamoto et al. |
| 4,837,267 A | 6/1989 | Malhotra |
| 4,840,998 A | 6/1989 | Shimizu |
| 4,879,362 A | 11/1989 | Morgan |

(Continued)

FOREIGN PATENT DOCUMENTS

| | | |
|---|---|---|
| EP | 1192957 A2 | 4/2002 |
| EP | 1 201 689 | 5/2002 |

(Continued)

OTHER PUBLICATIONS

International Search Report—PCT/US2010/000811 dated Jul. 27, 2010.
Fluoroplastics—vol. 1: Non-Melt Processible Fluoroplastics; Williams Andrew, Inc.; Norwich, NY at p. 19 (2000).
International Standard ISO 12086-1: 2006, Fluoropolymer dispersions and mounding and extrusion materials; Part 1: Designation system and basis for specifications, Geneva, Switzerland (2006).
Drobny, Technology of Fluoropolymers Second Edition; General Chemistry (7 pages).
Ebnesajjad, Sina; Fluoroplastics, PCL Handbook Series, vol. 1, Non-Melt Processible Fluoroplastics, The Definitive User's Guide and Databank; pp. 51-52.

(Continued)

*Primary Examiner* — Nicole M Buie-Hatcher
(74) *Attorney, Agent, or Firm* — Amy L. Miller

(57) ABSTRACT

A true tetrafluoroethylene (TFE) copolymer of the fine powder type is provided, wherein the copolymer contains polymerized comonomer units of at least one comonomer other than TFE in concentrations of at least or exceeding 1.0 weight percent, and which can exceed 5.0 weight percent, wherein the copolymer is expandable, that is, the copolymer may be expanded to produce strong, useful, expanded TFE copolymeric articles having a microstructure of nodes interconnected by fibrils. Articles made from the expandable copolymer may include tapes, membranes, films, fibers, and are suitable in a variety of end applications, including medical devices.

26 Claims, 3 Drawing Sheets

(56) References Cited

U.S. PATENT DOCUMENTS

| | | |
|---|---|---|
| 4,904,726 A | 2/1990 | Morgan |
| 4,952,630 A | 8/1990 | Morgan |
| 4,952,636 A | 8/1990 | Morgan |
| 5,064,593 A | 11/1991 | Tamaru et al. |
| 5,188,764 A | 2/1993 | Shimizu et al. |
| 5,230,937 A | 7/1993 | Effenberger |
| 5,266,639 A | 11/1993 | Chapman |
| 5,374,683 A | 12/1994 | Morgan |
| 5,397,829 A | 3/1995 | Morgan |
| 5,464,904 A | 11/1995 | Chapman |
| 5,494,752 A | 2/1996 | Shimizu |
| 5,506,281 A | 4/1996 | Muhlbauer |
| 5,547,551 A | 8/1996 | Bahar |
| 5,547,761 A | 8/1996 | Chapman |
| 5,599,614 A | 2/1997 | Bahar |
| 5,635,041 A | 6/1997 | Bahar |
| 5,637,663 A | 6/1997 | Anolick |
| 5,681,402 A | 10/1997 | Ichinose |
| 5,731,394 A | 3/1998 | Treat |
| 5,756,620 A | 5/1998 | Aten |
| 5,861,324 A | 1/1999 | Ichinose |
| 5,898,042 A | 4/1999 | Sawada et al. |
| 5,922,425 A | 7/1999 | Greuel |
| 5,922,468 A | 7/1999 | Huesmann |
| 5,925,705 A | 7/1999 | Araki |
| 5,972,449 A | 10/1999 | Chung |
| 6,025,092 A | 2/2000 | Doyle |
| 6,060,167 A | 5/2000 | Morgan |
| 6,071,600 A | 6/2000 | Rosenmayer |
| 6,103,361 A | 8/2000 | Batzar |
| 6,107,423 A | 8/2000 | Wheland |
| 6,114,028 A | 9/2000 | Muchin |
| 6,114,452 A | 9/2000 | Schmiegel |
| 6,127,486 A | 10/2000 | Burger |
| 6,133,389 A | 10/2000 | Anolick |
| 6,136,933 A | 10/2000 | Jones |
| 6,140,410 A | 10/2000 | Kolouch |
| 6,140,436 A | 10/2000 | Doyle |
| 6,143,675 A | 11/2000 | McCollam et al. |
| 6,156,453 A | 12/2000 | Shimizu et al. |
| 6,166,138 A | 12/2000 | Kolouch |
| 6,177,196 B1 | 1/2001 | Brothers |
| 6,177,533 B1 | 1/2001 | Woodward |
| 6,191,208 B1 | 2/2001 | Takahashi |
| 6,197,904 B1 | 3/2001 | Gangal |
| 6,211,319 B1 | 4/2001 | Schmiegel |
| 6,221,970 B1 | 4/2001 | Morken |
| 6,228,963 B1 | 5/2001 | Wheland |
| 6,232,372 B1 | 5/2001 | Brothers |
| 6,248,435 B1 | 6/2001 | Leck |
| RE37,307 E | 8/2001 | Bahar |
| 6,281,296 B1 | 8/2001 | MacLachlan |
| 6,287,702 B1 | 9/2001 | Kolouch |
| 6,291,054 B1 | 9/2001 | Thomas |
| 6,300,445 B1 | 10/2001 | Hung |
| 6,312,814 B1 | 11/2001 | Kolouch |
| 6,359,030 B1 | 3/2002 | Tsuda |
| RE37,656 E | 4/2002 | Bahar |
| RE37,701 E | 5/2002 | Bahar |
| 6,395,848 B1 | 5/2002 | Morgan |
| 6,403,213 B1 | 6/2002 | Huesmann |
| 6,403,758 B1 | 6/2002 | Loomis |
| 6,416,698 B1 | 7/2002 | Mertdogan |
| 6,423,798 B2 | 7/2002 | Wheland |
| 6,429,258 B1 | 8/2002 | Morgan |
| 6,472,594 B1 | 10/2002 | Ichinose |
| 6,486,280 B1 | 11/2002 | Anolick |
| 6,509,429 B1 | 1/2003 | Kitaichi |
| 6,518,349 B1 | 2/2003 | Felix |
| 6,518,381 B2 | 2/2003 | Kobayashi |
| 6,538,058 B2 | 3/2003 | Kobayashi |
| 6,541,589 B1 | 4/2003 | Baillie |
| 6,551,708 B2 | 4/2003 | Tsuda |
| 6,582,628 B2 | 6/2003 | Kondo |
| 6,592,977 B2 | 7/2003 | Thomas |
| 6,638,999 B2 | 10/2003 | Bish |
| 6,689,833 B1 | 2/2004 | Bidstrup |
| 6,730,762 B2 | 5/2004 | Lousenberg |
| 6,750,294 B2 | 6/2004 | Sugiyama |
| 6,761,964 B2 | 7/2004 | Tannenbaum |
| 6,770,404 B1 | 8/2004 | Wheland |
| 6,803,419 B2 | 10/2004 | Tsuda |
| 6,803,437 B2 | 10/2004 | Kobayashi |
| 6,806,332 B2 | 10/2004 | Royer |
| 6,822,059 B2 | 11/2004 | Buckanin |
| 6,822,060 B2 | 11/2004 | Kobayashi |
| 6,824,930 B1 | 11/2004 | Wheland |
| 6,833,418 B2 | 12/2004 | Tan |
| 6,841,594 B2 | 1/2005 | Jones |
| 6,870,020 B2 | 3/2005 | Aten |
| 6,914,105 B1 | 7/2005 | Charpentier |
| 6,921,606 B2 | 7/2005 | Sassa et al. |
| 6,956,078 B2 | 10/2005 | Cavanaugh |
| 7,049,365 B2 | 5/2006 | Uschold |
| 7,063,839 B2 | 6/2006 | Royer |
| 7,064,170 B2 | 6/2006 | Kaspar |
| 7,084,225 B2 | 8/2006 | Baillie |
| 7,531,611 B2 | 5/2009 | Sabol et al. |
| 8,637,144 B2 * | 1/2014 | Ford ............................. 428/304.4 |
| 8,911,844 B2 * | 12/2014 | Ford ............................. 428/36.5 |
| 9,040,646 B2 * | 5/2015 | Ford ............................. 526/247 |
| 2005/0220848 A1 | 10/2005 | Bates |
| 2006/0148912 A1 | 7/2006 | Katsurao et al. |

FOREIGN PATENT DOCUMENTS

| | | |
|---|---|---|
| EP | 1 746 130 | 1/2007 |
| GB | 2 337 991 | 12/1999 |
| JP | 56 92943 | 7/1981 |
| JP | 59-82144 | 4/1983 |
| JP | 10-243976 | 12/1997 |
| JP | 11-240918 | 9/1999 |
| JP | 2003-192815 | 7/2003 |
| JP | 2005-306033 | 3/2004 |
| JP | 2007-514481 | 6/2007 |
| JP | A 2010-527972 | 12/2010 |
| WO | WO 97/36952 | 10/1997 |
| WO | WO 99/07307 | 2/1999 |
| WO | WO 2007/005361 | 1/2007 |
| WO | WO 2009/045423 | 4/2009 |

OTHER PUBLICATIONS

2010 Fluorotherm Polymers, Inc. powered by WebiMax.com http://Flurotherm.com/Properties-Physical.asp Comparison of Materials, Typical Properties of Fluoropolymers; 2010.

Ebnesajjad, S. (2000), Fluoroplastics, vol. 1—Non-Melt Processible Fluoroplastics. William Andrew Publishing/Plastics Design Library. Preface and Chapter 3, pp. 33-38. Online version available at: http://www.knovel.com/we/portal/browser/display?_EXT_KNOVEL_DISPLAY_bookid=64&VericalID-0.

"Olefin (chemical compound)", Encylcopedia Brittanica, Encyclopedia Brittancia Online, Encylcopedia Brittanica Inc., 2013.

* cited by examiner

EXPANDABLE TFE COPOLYMERS, METHOD OF MAKING, AND POROUS, EXPANDED ARTICLES THEREOF

BACKGROUND OF THE INVENTION

The invention relates to fluorocopolymers, as defined herein to denote any fluoropolymer containing tetrafluoroethylene monomer units and at least or more than 1.0% by weight of units of at least one other comonomer,* polymerized to produce an expandable tetrafluoroethylene copolymer of the fine powder type. A process of polymerization of these monomers is described, as well as the porous products produced by expansion (stretching under controlled conditions) of the aforesaid copolymers.

* See, e.g., Fluoroplastics—Vol 1: Non-Melt Processible Fluoroplastics; Williams Andrew, Inc., Norwich, N.Y., at p. 25 19 (2000); see, also, ISO 12086.

Techniques for the dispersion polymerization of tetrafluoroethylene (TFE) monomer are known. Dispersion polymerization of TFE produces a resin that has come to be known as "fine powder". See, e.g., U.S. Pat. No. 4,016,345 (Holmes, 1977). In such processes, generally, sufficient dispersing agent is introduced into a water carrier such that, upon addition of tetrafluoroethylene monomer in the presence of a suitable polymerization initiator and, upon agitation and under autogenous tetrafluoroethylene pressure of 10 to 40 kg/cm$^2$, the polymerization proceeds until the level of colloidally dispersed polymer particles is reached and the reaction is then stopped.

In contrast, particulate tetrafluoroethylene resins have also been produced by a process of suspension polymerization wherein tetrafluoroethylene monomer is polymerized in a highly agitated aqueous suspension in which little or no dispersing agent is employed. The type of particles produced in suspension polymerization has been termed "granular" resin or "granular powder". See, e.g., U.S. Pat. No. 3,655,611 (Mueller, 1972).

For both polymerization processes, copolymerization of tetrafluoroethylene with various fluorinated alkyl ethylene comonomers has been described. See, for example, U.S. Pat. No. 4,792,594 (Gangal, et al., 1988). However, the present invention relates, specifically, to the aqueous dispersion polymerization technique, in which the product of the polymerization reaction is the copolymer of the invention dispersed within an aqueous colloidal dispersion. In this process, tetrafluoroethylene monomer is pressured into an autoclave containing water and polymerization initiators, along with paraffin wax to suppress coagulum formation and an emulsifying agent. The reaction mixture is agitated and the polymerization is carried out at suitable temperatures and pressures. Polymerization results in the formation of an aqueous dispersion of polymer particles, and the dispersed polymer particles may subsequently be coagulated by techniques known in the art to obtain what has become known as the fine powder form of the polymer.

Various prior patents have disclosed techniques for the homopolymerization of tetrafluoroethylene and for the polymerization of TFE with small amounts (<1.0% by weight) of other monomers. Among those are included U.S. Pat. No. 4,576,869 (Malhotra, 1986) and U.S. Pat. No. 6,177,533B1 (Jones, 2001).

Fine powder resins are known to be useful in paste extrusion processes and in stretching (expansion) processes in which the paste-extruded extrudate, after removal of extrusion aid lubricant, is stretched to produce porous, strong products of various cross-sectional shapes such as rods, filaments, sheets, tubes, etc. Such a stretching process is disclosed in the pioneering U.S. Pat. No. 3,953,566 (Gore, 1976), assigned commonly with the instant invention.

The expansion process as it applies to fluorocarbon polymers is fully described in the aforesaid '566 patent, and that process has come to identify what is currently termed the "expanded" form of TFE fluoropolymers, and will serve to define what is meant herein as an expanded or expandable TFE polymer or copolymer.

The term "copolymer" as it has been used in connection with fluoropolymers in the prior art has been inconsistently applied. For all purposes herein, as set out in the *Fluoroplastics* text cited above and in the ISO 12086 classification cited above, the normal convention of polymer science will be followed, and the term "copolymer" will apply to any fluoropolymer containing more than 1.0% by weight of at least one comonomer in addition to TFE. A fluoropolymer containing less than 1.0% comonomer is properly categorized as a "modified" homopolymer (Id.), although the term "copolymer" has been misapplied in the literature when referring, in fact, to "modified" homopolymers. One must examine each particular instance of such use to determine the actual concentrations of comonomers employed to determine whether, in fact, the referenced composition is a "modified" homopolymer or a true copolymer, that is, whether or not the polymeric product, in fact, contains more than 1.0 weight percent comonomeric units.

By definition herein, the invention provides a true TFE copolymer, of the fine powder type, that is expandable, as defined above, to produce useful, expanded TFE copolymeric products.

U.S. Pat. No. 4,837,267 (Malhotra, 1989) discloses a three-component composition termed "core-shell TFE copolymers", which are described as non-melt processable, including chlorotrifluoroethylene (CTFE) monomer residing in the core and having recurring units of a comonomer of perfluoro (n-alkylvinyl) ether of 3-7 carbon atoms (col. 1, lines 45-55). The total comonomer content in the particles is said to be between 0.001 and 2 weight percent. The examples presented all relate to terpolymers having comonomeric concentrations much less than the range described, namely 0.23% CTFE and 0.0145% PPVE (total of 0.2445 wt %) in Example 1, and 0.13% HFP and a minute, undeterminable amount of PPVE in Example 2. The stated upper limit of 2% is therefore unsupported by the specification and examples presented. Moreover, there is no disclosure or suggestion in the '267 patent of an expanded or an expandable TFE copolymeric composition.

Japanese Patent Application (Kokai) 2005-306033A, published Nov. 4, 2005, discloses thin films of PTFE which are said to be non-porous, non-gas-permeable (p. 5), and to contain "trace monomer units" in the range of 0.001-2 mol % (p. 7) described as "modified" PTFE. The objective of the invention is said to be obtained by "heat treatment" of "porous PTFE resin film" to render the film "substantially nonporous". There is no disclosure or suggestion in this reference of a porous, expandable TFE copolymeric composition.

U.S. Pat. No. 4,391,940 (Hoechst, 1983) discloses and describes a partially modified tetrafluoroethylene polymer having a "three-shell" particle structure. The resins are said to be suitable for paste extrusion to produce cable insulation and highly stretchable, unsintered tapes (940 patent, Abstract). This patent describes fluorinated modifying monomers which are capable of copolymerizing with tetrafluoroethylene, such as perfluoropropene, perfluoroalkyl vinyl ether, and halogen-substituted or hydrogen-substituted fluoroolefins. The specification cautions that the total amount of the comonomer modifying agent should be so low that the specific properties of the pure polytetrafluoroethylene are retained, that is, there remains no possibility of processing from the melt because of the extremely high melt viscosity for such modified polymers. (940 patent, col. 1, I. 62 et seq.) Products disclosed include modified polymer particles having a core of a polymer of "0.05 to 6% by weight" of at least one modifying fluoroolefin comonomer, a first, inner shell, immediately adjacent the core, of TFE units, and a second, outer shell, immediately adjacent the inner shell, of a polymer comprising "0.1 to 15% by weight" of units of at least one modifying fluoroolefin (col. 3, I. 5, et seq.). Examples of the "three-shell" products provided in this reference for illustration of the principles disclosed therein show that tapes, upon stretching, after removal of lubricant, developed defects or tore completely at relatively modest stretch ratios. For example, the detailed procedure described in EXAMPLE 31, at col. 14, I. 60 to col. 16, I. 6, produced a product which developed defects at a 4:1 stretch ratio and tore completely at a stretch ratio of 8:1 (940 patent, Table III).

For comparison and to place various of the prior art disclosures in context, recently issued U.S. Pat. No. 6,841,594 (Jones, 2005) instructs that polytetrafluoroethylene (PTFE) refers to the polymerized tetrafluoroethylene by itself without any significant comonomer present, and that "modified" PTFE refers to TFE polymers having such small concentrations of comonomer that the melting point of the resultant polymer is not substantially reduced below that of PTFE. The concentration of such comonomer, consistent with prior citations above, is preferably less than 1 weight %, more preferably less than 0.5 weight %. The modifying comonomers cited include, for example, hexafluoropropylene (HFP), perfluoro(methyl vinyl ether) (PMVE), perfluoro (propyl vinyl ether) (PPVE), perfluoro (ethyl vinyl ether) (PEVE), chlorotrifluoroethylene (CTFE), perfluoro-butyl ethylene (PFBE), or other monomer that introduces side groups into the molecule. These instructions are consistent with the disclosures above and with the definitions contained herein, i.e., that the term "copolymer", as contrasted with the term "modified homopolymer", shall mean any fluoropolymer containing more than 1.0% by weight of at least one comonomer in addition to TFE.

U.S. Pat. No. 6,127,486 (Burger, et. al., 2000) discloses a blend of a fluoropolymer and a "thermoplastic", wherein the "thermoplastic" is said to include a "PTFE copolymer" (col. 4, I. 46). The specification instructs that, for the resins described therein, the amount of comonomer is limited such that the [modified] PTFE exhibits properties of "not being processable in the melt." (Emphasis in original). The PTFE is referred to as modified PTFE "in which the comonomers are contained in an amount below 2, preferably 1 wt. % in PTFE." (Col. 4, I. 50) No examples are provided of any copolymer having greater than 1.0 weight % of an additional comonomer, and the patent concerns blends of polymers, a different physical form entirely from the true copolymers which form the subject matter of the present invention.

Another recent reference, Japanese Patent Application No. 10-243976 (Asahi Glass Co., Ltd., claiming priority to Dec. 26, 1997) is still further instructive of the state of the art in the field of copolymers and modified homopolymers of TFE. That patent application, titled "Tetrafluoroethylene Copolymer and Application Thereof", contains claims to polymers having, inter alia, additional comonomer content in the range of 0.005 to 0.05 mol % (about 0.012 to 0.123 wt %). The patent discusses known copolymerization techniques and discloses that a further, related Japanese application, JP (Kokoku) 3-66926, proposes a method for modifying PTFE by employing $R_f$—CH=CH$_2$ (where $R_f$ is a $C_{1-10}$ perfluoroalkyl group) as a comonomer. In the proposed method, the comonomer is continuously added during the polymerization process in order to enhance modification in the initial period. The modification is said to be primarily performed in order to improve the paste extrudability of fine powders, for example, to reduce extrusion pressure, and the content of polymerization units based on comonomers, while less than 0.5 wt %, is "still comparatively high in substantial terms" (0.1 wt % or higher). Consequently, the product has substantially no melt moldability and possesses markedly reduced crystallinity. The reference describes "another drawback", that such modified PTFE becomes less heat resistant because of the structure of the comonomers introduced. Finally, the Asahi patent application concludes, quoting therefrom:

In addition, the comonomer structure impairs molecular orientation, causing breakage during stretching and making the product substantially unusable for the manufacture of stretched porous articles.

An object of the present invention is to provide a PTFE product that has excellent extrudability, can be uniformly stretched, and yields high-strength porous articles.

This objective is then said to be obtained by limiting the introduction of polymerization units based on comonomers copolymerizable with TFE to an amount that has no discernible effect on processability.

Specifically, the Asahi application provides a product of TFE and a fluorinated comonomer expressed by the general formula $CH_2$=CH—$R_f$ (where $R_f$ is a $C_{1-10}$ perfluoroalkyl group, wherein this polymer contains 0.005 to 0.05 mol % polymerization units based on the fluorinated comonomer. Further, a porous polymer article is provided, obtained by a process in which a powder composed of the aforementioned modified PTFE is paste-extruded and then stretched at a temperature of 250° C. or higher. This reference, however, specifically cautions against polymerization in which the amount of copolymerized monomer exceeds certain limits. The application states, again quoting directly:

The content of the polymerization units based on fluorinated comonomer in the present invention must be rigorously controlled because of considerations related to stretchability. The content of the units in the PTFE must fall within a range of 0.005 to 0.05 mol %. A content above 0.05 mol % brings about a slight reduction in polymer crystallinity, results in a lower paste extrusion pressure, and has a markedly adverse effect on stretchability. A content below 0.005 mol % makes it substantially more difficult to improve the physical properties of a stretched article or to obtain other modification effects. A range of 0.01 to 0.04 mol % is particularly preferred.

This, again, is consistent with the other teachings of the prior art references discussed hereinabove. In Example 4 of this Asahi reference, in which a "high" content (by applicant's definition), 0.42 wt %, of perfluorobutylethylene comonomer was employed, the paste extrusion pressure was desirably low, and "excellent" extrudability was obtained. However, a test specimen, on stretching, broke. The specification discloses, at this "high" level of comonomer concentration of 0.42 wt %, " . . . breakage occurred during stretching, and it was impossible to obtain a porous article." (p. 12, §0050). In spite of these cautionary teachings, and in contrast thereto, the present invention is directed to true TFE copolymers, all containing in excess of 1.0 weight percent comonomer units, all of which are expandable to form porous expanded articles, to a process for their manufacture, and to the expanded articles produced thereby. No known prior art reference discloses or suggests such porous, expanded copolymeric articles or the resins from which they are produced.

It is wholly unexpected, and contrary to prior art teachings, that a TFE copolymer, having comonomeric unit concentrations in the high ranges claimed herein, can be expanded as disclosed hereinbelow, to and beyond a 25:1 stretch ratio, to form a uniform, viable shaped article. This synergistic result is truly surprising to one skilled in this art.

SUMMARY OF THE INVENTION

A process is provided for the copolymerization of an expandable tetrafluoroethylene (TFE) copolymer of the fine powder type, the copolymer containing 99.0% or less by weight tetrafluoroethylene (TFE) monomer units and at least, or greater than, 1.0% by weight, of units of at least one other comonomer, that is, other than tetrafluoroethylene. The other comonomer is an ethylenically unsaturated comonomer having a sufficiently high reactivity ratio to TFE to enable polymerization therewith. The process includes the steps of copolymerizing the TFE monomer and the at least one other monomer in a pressurized reactor by feeding 99.0% or less by weight of the TFE monomer into the reactor, feeding at least or greater than 1.0% by weight of the other comonomer into the pressurized reactor, wherein percentages are based upon total weight of monomers fed, initiating polymerization of the monomers with a free radical initiator, and stopping the feeding of the other monomer at a point in time in the polymerization reaction prior to completion of the reaction. In one embodiment, optionally, excess comonomer is removed (evacuated) from the reactor, as needed, prior to completion of the reaction. The at least one other comonomer may be an olefin such as ethylene, propylene or isobutylene, a fluorinated monomer selected from the group consisting of chlorotrifluoroethylene (CTFE), hexafluoropropylene (HFP), vinylidene fluoride (CFH=CH$_2$), vinylidene difluoride (CF$_2$=CH$_2$), hexafluoroisobutylene (HFIB) and trifluoroethylene (CF$_2$=CFH), a fluorodioxole of the general formula:

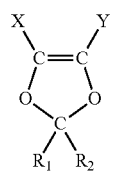

wherein R$_1$ and R$_2$=F or a 1-3 carbon alkyl group containing at least one fluorine, and X, Y may be F 10 and/or H;

a fluorodioxole of the general formula:

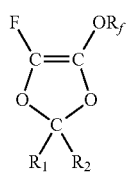

wherein R$_f$ is a perfluoroalkyl carbon of 1-5 atoms, and R$_1$, R$_2$ may be F and/or CF$_3$; and a fluorodioxalane of the general formula:

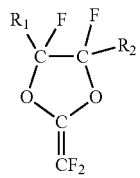

wherein R$_1$, R$_2$ may be F and/or a perfluoroalkyl carbon of 1-5 atoms. Alternatively, the at least one other comonomer may be a perfluoroalkyl ethylene monomer such as a monomer selected from the group perfluorobutylethylene (PFBE), perfluorohexylethylene (PFHE) and perfluoro-octylethylene (PFOE), or it may be a perfluoroalkyl vinyl ether monomer such as a monomer selected from the group consisting of perfluoro(methyl vinyl ether) (PMVE), perfluoro(ethyl vinyl ether) (PEVE), and perfluoro(propyl vinyl ether) (PPVE). More than one other comonomer may be fed into the pressurized reactor, to produce multicomponent copolymers, i.e., terpolymers, etc.

The monomer feeds may be introduced as a precharge in the polymerization, or the at least one other comonomer may be introduced incrementally or intermittently during the reaction.

The process in one embodiment preferably includes stopping the feeding of the at least one other comonomer at less than 90% of the reaction completion.

Higher concentrations of comonomer in the copolymer produced are achieved by feeding the at least one other comonomer at higher concentration levels, such as at least 1.5% by weight, at least 2.0% by weight, and exceeding 5.0% by weight of the at least one other comonomer to the reactor.

The aforesaid process produces an expandable tetrafluoroethylene (TFE) copolymer of the fine powder type containing 99.0% or less by weight of polymerized tetrafluoroethylene (TFE) monomer units and at least, or greater than, 1.0% by weight, of polymerized comonomer units of the at least one other comonomer fed into the reaction, based on total weight of polymer produced. This true copolymer is expandable to a porous, expanded copolymeric material having a microstructure characterized by nodes 1 interconnected by fibrils 2, as shown in FIG. 1, described more fully below. Further views of alternative unique node, 1, and fibril, 2, microstructures are shown in FIGS. 2 and 3.

The expandable copolymer produced contains at least one other polymerized comonomer within the following group: olefins such as ethylene, propylene and isobutylene; fluorinated comonomers such as chlorotrifluoroethylene (CTFE), hexafluoropropylene (HFP), vinylidene fluoride (CFH=CH$_2$), vinylidene difluoride (CF$_2$=CH$_2$), hexafluoroisobutylene (HFIB), trifluoroethylene (CF$_2$=CFH), fluorodioxoles and fluorodioxalanes; and perfluoroalkyl ethylene monomers, including perfluorobutylethylene (PFBE), perfluorohexylethylene (PFHE) and perfluorooctylethylene (PFOE), and a perfluoroalkyl vinyl ether monomer, including perfluoro(methyl vinyl ether) (PMVE), perfluoro(ethyl vinyl ether) (PEVE), and perfluoro(propyl vinyl ether) (PPVE). The copolymer produced may include more than one other polymerized comonomer, and the comonomer content in the copolymer always exceeds 1.0% by weight, may exceed 1.5% by weight polymerized units of the other comonomer and, indeed, may exceed 5.0 weight % of polymerized units of the other comonomer(s).

In a further embodiment of the invention, copolymer materials are produced which exhibit unique adhesion characteristics which cannot be achieved in PTFE homopolymers. That is, the copolymer can be adhered to itself or other materials after subjecting it to lower temperature and/or shorter time and/or lower pressure than what is required for adhering PTFE homopolymer to itself. For example, as described later herein with respect to room temperature adhesion testing, this adhesion, or bonding, can be achieved at temperatures at or below about 290° C. with these unique copolymers (hence, at lower temperatures than required for PTFE homopolymers).

The copolymer of the invention is produced in the form of fine particles dispersed within an aqueous medium which may be coagulated using known techniques to produce fine powder resins. Porous, expanded TFE copolymer materials having a microstructure of nodes interconnected by fibrils are further provided according to the invention. These porous, expanded copolymeric materials can be produced in the form of shaped articles such as sheets or films, tubes, rods, and continuous filaments, and these articles are generally strong, that is, their matrix tensile strengths in at least one direction exceed 5,000 psi. Matrix tensile strengths in at least one direction can, for certain products, exceed 30,000 psi, thus providing extremely strong, porous, true copolymeric expanded TFE articles useful in many applications.

The copolymer of the invention is produced in the form of fine particles dispersed within an aqueous medium which may be coagulated using known techniques to produce fine powder resins. Porous, expanded TFE copolymer materials having a microstructure of nodes interconnected by fibrils are further provided according to the invention. These porous, expanded copolymeric materials can be produced in the form of shaped articles such as sheets or films, tubes, rods, and continuous filaments, and these articles are generally strong, that is, their matrix tensile strengths in at least one direction exceed 5,000 psi. Matrix tensile strengths in at least one direction can, for certain products, exceed 30,000 psi., thus providing extremely strong, porous, true copolymeric expanded TFE articles useful in many applications. In a further embodiment, such expanded TFE materials may be compressed or otherwise processed to achieve a reduction in porosity utilizing processing techniques known in the art.

The copolymer of the present invention can be used in a wide variety of medical and commercial devices. Medical devices include the incorporation of the inventive copolymer into long and short term implantable devices, as well as in disposable, or single use, supplies and devices. These devices include, but are not limited to, vascular grafts (to repair, replace, bypass or augment a blood vessel or another vascular graft), other shunting conduits, surgical and laparoscopic sheets and patches, endoluminal prostheses (e.g., stent-grafts), components of cell containment devices, and substrates for drug delivery, catheters, space filling or augmentation devices, joint spacers, surface coatings for devices, lenses, work surface or clean room surface coatings, seals, gaskets, blood contact surfaces, bags, containers and fabric liners.

BRIEF DESCRIPTION OF THE DRAWINGS

In the accompanying drawings.

DESCRIPTION OF THE INVENTION

Figure 1:
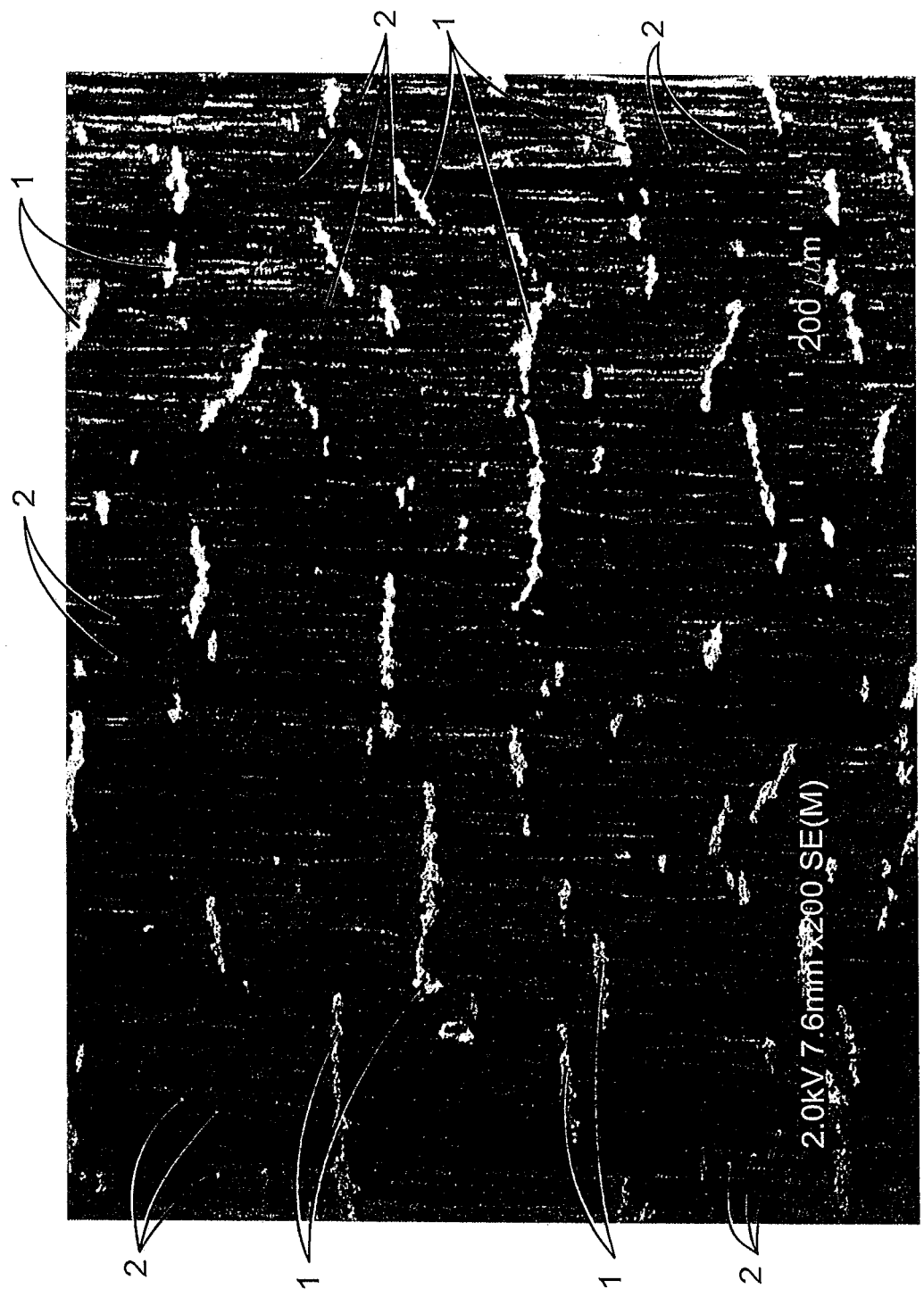
FIG. 1, is a SEM photomicrograph of an expanded sheet of a copolymeric resin produced according the invention herein, taken at 200× magnification, showing the node 1 and fibril 2 microstructure of this material, the respective nodal intersections being interconnected by the multiplicity of fibrils 2.

A process for the polymerization of a true tetrafluoroethylene (TFE) copolymer of the fine powder type is provided, wherein the copolymer contains polymerized comonomer units of at least one comonomer other than TFE in concentrations of at least or exceeding 1.0 weight percent, and which can exceed 5.0 weight percent, wherein the copolymer is expandable, that is, the copolymer may be expanded to produce strong, useful, expanded TFE copolymeric articles having a microstructure of nodes interconnected by fibrils.

The copolymer of this invention is produced by a polymerization process wherein the copolymerization reaction is started by a suitable initiator, after which initiator addition is stopped, allowing the reaction to slow down and proceed to completion, at a point between 15% and 90% of the progression of the reaction toward completion. Preferably the initiator addition is stopped at about the mid-point of the reaction, i.e., at 20-60% to completion.

Substantially non-telogenic dispersing agents are used. Ammonium perfluoro octanoic acid (APFO or "C-8") is one acceptable dispersing agent. Programmed addition (pre-charge and pumping) is known and is preferred. Attention must be paid to ingredient purity to achieve the desired properties in polymerizations as described herein. Ionic impurities, which can increase ionic strength, in addition to soluble organic impurities, which can cause chain transfer or termination, must be minimized. It is clearly important to employ ultra pure water in all such polymerization reactions.

The break strength associated with an extruded and expanded (stretched) TFE polymeric beading produced from a particular resin is directly related to that resin's general suitability for expansion, and various methods have been employed to measure break strength. The following procedure was used to produce and test expanded beading specimens made from the copolymers of this invention, the data for which are reported hereinbelow.

For a given resin, 113.4 g of fine powder resin is blended together with 130 cc/lb (24.5 g) of Isopar® K. The blend is aged for about 2 hours at 22° C. in a constant temperature water bath. A 1-in. diameter cylindrical preform is made by applying about 270 psig of preforming pressure for about 20 seconds. The preform is inspected to ensure it is crack free. An extruded beading is produced by extruding the preformed, lubricated resin through a 0.100 in. diameter die having a 30 degree included inlet angle. The extruder barrel is 1-in, in diameter and the ram rate of movement is 20 in./min. The extruder barrel and die are at room temperature, maintained at 23° C., plus or minus 1.5° C. The Isopar K is removed from the beading by drying it for about 25 minutes at 225-230° C. Approximately the first and last 8 ft. of the extruded beading are discarded to eliminate end effects. A 2.0 in. section of the extruded beading is expanded by stretching at 290° C. to a final length of 50 in. (expansion ratio of 25:1) and at an initial rate of stretch of 100% per second, which is a constant rate of 2 in. per second. Approximately a 1 ft. length from near the center of the expanded beading is removed, and the maximum break load of the removed sample held at room temperature (23° C. plus or minus 1.5° C.) is measured using an Instron® tensile tester using an initial sample length of 2 in and a crosshead speed of 12 in/min. Measurements in duplicate are obtained and reported as the average value for the two samples. This procedure is similar to that described in U.S. Pat. No. 6,177,533B1, The expansion here is carried out at 290° C. instead of 300° C.

Figure 2:
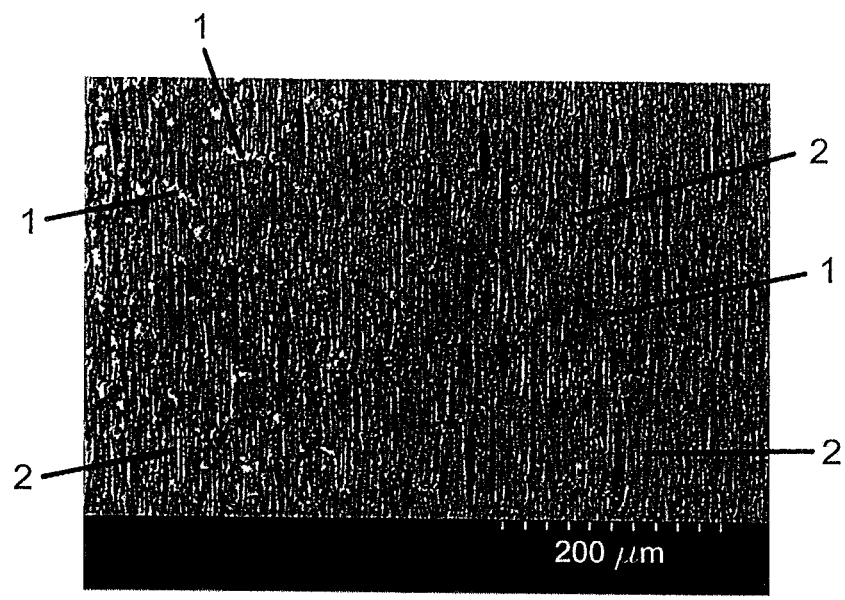
FIG. 2 is a SEM photomicrograph of the expanded beading specimen of the copolymeric resin produced in Example 6, taken at 200× magnification, showing the node 1 and fibril 2 microstructure of this material, the respective nodal intersections being interconnected by the multiplicity of fibrils 2.
Figure 3:
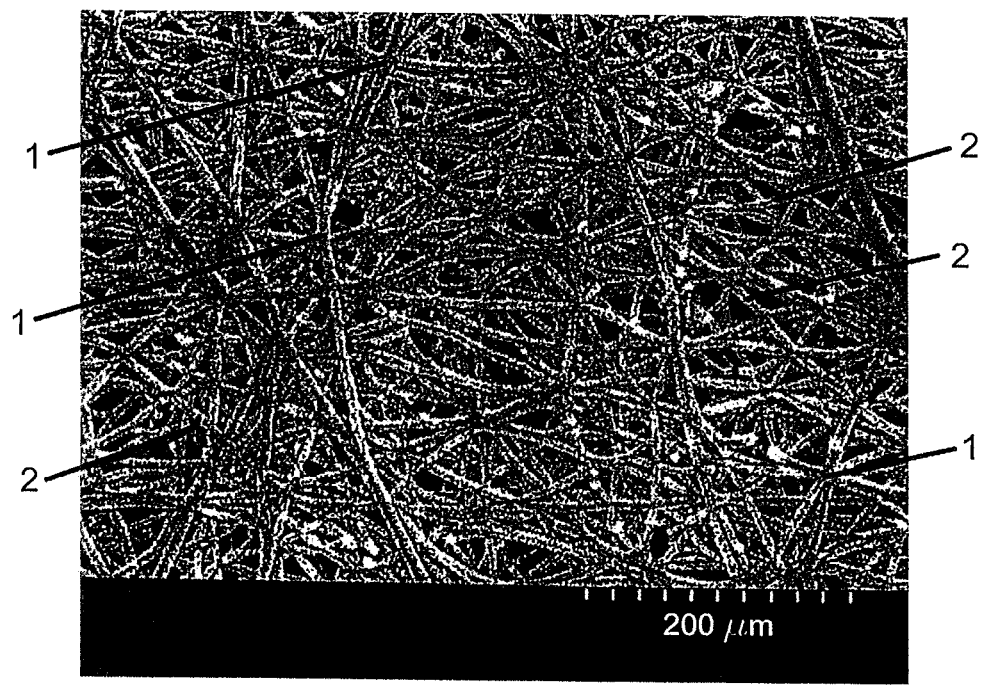
FIG. 3 is another SEM photomicrograph of the expanded sheet specimen of the copolymeric resin produced in Example 6, taken at 20,000× magnification, showing a node 1 and fibril 2 microstructure.

Core-shell resin structures containing polymerized monomers additional to TFE, structurally similar to those produced by the techniques described herein, and as described earlier herein, have been known for some time. See, e.g., U.S. Pat. No. 4,576,869 (Malhotra), U.S. Pat. No. 6,541,589B1 (Baillie) and U.S. Pat. No. 6,841,594B2 (Jones). In the examples which follow, and for the claimed compositions, the resins produced according to the present invention are all true copolymers, i.e., comonomer content exceeding 1.0 weight percent, verified using solid state NMR spectroscopy, as well as mass balance and detection of residual monomer in the gas phase of the polymerization batch, through gas chromatography. The compositions are all expandable to a stretch ratio of at least 25:1, to form expanded copolymeric articles having their unique node, 1, and fibril, 2, microstructure as shown in FIG. 1, verifiable through SEM examination, as demonstrated below. Further views of alternative unique node, 1, and fibril, 2, microstructures are shown in FIGS. 2 and 3.

Characterization of copolymer materials can be performed via standard analytical techniques available in the art including, but not limited to, DCS, NMR (including fluorine, proton, carbon and other known NMR techniques), TGA, IR, FTIR, Raman spectroscopy, and other suitable techniques.

TESTS

Differential Scanning Calorimetry (DSC)

This test was performed using a TA Instruments Q2000 DSC and TA Instruments standard aluminum pans and lids for Differential Scanning calorimetry (DSC). Weight measurements were performed on a Sartorius MC 210P microbalance.

Calibration of the Q2000 was performed by utilizing the Calibration Wizard available through the Thermal Advantage software supplied with the device. All calibration and resulting scans were performed under a constant nitrogen flow of 50 ml/min.

The sample was loaded info the pan and the weight was recorded to 0.01 mg precision, with samples ranging from 5.00 mg to 10.00 mg. These values were entered into the Thermal Advantage control software for the Q2000. The lid was placed on the pan and crimped using a standard press. A similar pan for reference was prepared, with the exception of the sample article, and its weight was also entered into the software. The pan containing the sample article was loaded onto the sample sensor in the Q2000 and the empty pan was loaded onto the reference sensor. The samples were then equilibrated at −50° C. and ramped at 20° C./min to 400° C. Data were analyzed using Universal Analysis 2000 v.3.9A from TA Instruments.

Adhesion Testing

Extruded PTFE tapes were cut into rectangles with dimensions of 20 mm width×75 mm length and were thermally bonded in a Carver press model #3895, from Fred S. Carver Inc, Wabash, Ind. to aluminum foil substrates to create 90 degree peel samples. The tapes were bonded to 23 micron thick Heavy Strength aluminum foil from Reynolds Consumer Products Co, Richmond, Va. 23230. Polyimide release film, Upilex grade 25SDADB, 25 microns thick, available from UBE Industries, LTD., Tokyo, Japan was used to prevent adhesion to the press plates and provide a pre-crack to initiate peel during 90 degree peel testing. Melt press time, and normal force were 30 minutes and 450 Kg. Samples were prepared at melt press temperatures of 195° C., 290° C., and 350° C. Once bonded the samples were cooled while still under pressure to approximately 21° C. for approximately 20 minutes. Foil-PTFE tape peel samples at each bonding temperature were prepared simultaneously to maintain a common thermal history. A 90 degree peel test is conducted at a test speed of 1 mm/sec using an Imass SP-2000 Slip-Peel Tester, available from Instrumentors Inc., Strongsville, Ohio. Results were reported in $J/m^2$, and any measurable value defined that the material exhibits adhesion. For samples where the sample fell apart prior to testing, a "no adhesion" value was reported.

NMR Analysis

A sample of 10 to 25 mg was packed into a 2.5 mm ZrO spinner using standard Bruker 2.5 mm packing accessories (Bruker BioSpin Inc., Boston, Mass.). $^{19}F$ spectra were collected at about 296 Kelvin on a Bruker-BioSpin 2.5 mm cross polarization magic angle spinning (CPMAS) probe positioned in a standard bore 7.05 T Bruker ultra shielded superconducting magnet. The samples were positioned at the magic angle and spun at 32.5 kHz. A Bruker BioSpin Avance II 300 MHz system was used to collect $^{19}F$ NMR data at 282.4 MHz. Software used for data acquisition and data processing was Topspin 1.3. The data was collected using the conditions specified in Table B. The spectra were externally referenced to PTFE at −123 ppm.

Table A

NMR Instrument Used

TABLE A

NMR Instrument Used

| | |
|---|---|
| Manufacturer | Bruker BioSpin |
| Model | Avance II 300 MHz |
| Magnet | 7.05 T Ultrashielded |
| Probe | Bruker 2.5 mm CPMAS Multinuclear |
| Rotor | Standard Bruker 2.5 mm |
| $^{19}F$ Frequency | 282.4 MHz |
| Software | Topspin 1.3 |

TABLE B

NMR Acquisition Parameters

| Parameter | Value |
|---|---|
| MAS Spinning speed | 32.5 kHz |
| Pulse length (11°) | 0.4 □s |
| Spectral Window | 113636 Hz (402 PPM) |
| Transmitter offset | −100 PPM |
| Number of scans | 2000 |
| Recycle delay | 3 s |
| Acquisition Time | 150 ms |
| Acquired Data Points used in Fourier Transform | 8000 |
| Zero Fill before Fourier Transform | 32k |
| Line broadening | 15 Hz |

The following examples are intended to be illustrative of the invention, but are not to be construed as limiting the scope of the invention in any way.

EXAMPLE 1

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83 C and agitated at 60 rpm. Subsequently, 0.8 MPa of VDF was added followed by addition of TFE until the pressure reached 2.8 MPa. At this time, KMNO4 in a DI water solution (0.063 g/L) was injected at 80 mL/min until approximately 2 kg of TFE was added. After addition of the 2nd Kg of TFE, the pressure in the reactor was reduced to 50 Kpa using vacuum and pressurized with fresh TFE to 2.8 MPa. The KMnO4 was added at 20 mL/min for the 3rd Kg of TFE and further reduced to 10 mL/min for the 4th Kg of TFE. After the 4th Kg of TFE was added, KMnO4 was no longer added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 14.3 Kg of TFE had been added to the reactor. The weight of the dispersion produced was 44.73 Kg containing 32.6% solids. The dispersion was coagulated with Nitric acid and dried at 170° C. The raw dispersion particle size (RDPS) of the polymer particle was 0.296 microns and the standard specific gravity was 2.156. The VDF concentration in the copolymer was measured to be 3.48 mol % (2.26 wt %). The break strength of the beading was 6.6 lbs.

The matrix tensile strength of the specimen was measured to be 37,299 psi.

EXAMPLE 2

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83° C. and agitated at 60 rpm. Subsequently, 0.8 MPa of trifluoroethylene (herein designated TrFE) was added followed by addition of TFE until the pressure reached 2.8 MPa. At this time, KMnO4 in a DI water solution (0.1 g/L) was injected at 80 mL/min until approximately 0.5 kg of TFE was consumed. At this time, the rate was reduced to 40 mL/min until a second Kg of TFE was consumed. The pressure in the reactor was reduced to 50 Kpa using vacuum and pressurized with fresh TFE to 2.8 MPa. The KMnO4 was again added at 40 mL/min for the next 0.5 Kg of TFE and continued until 4 Kg of TFE was consumed. After 4 Kg of TFE was consumed, KMnO4 was no longer added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 45.74 Kg containing 35.8% solids. The dispersion was coagulated with Nitric acid and dried at 170 C.

The raw dispersion particle size (RDPS) of the polymer particle was 0.283 microns and the standard specific gravity was 2.213. The trifluoroethylene concentration in the copolymer was measured to be 3.2 mol % (2.6 wt %). The break strength of the beading specimen was 7.24 lbs.

The matrix tensile strength of the specimen was measured to be 28,602 psi.

EXAMPLE 3

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

To the evacuated reactor, 8 mL of PFBE was charged, and the reactor was heated to 83° C. and agitated at 60 rpm. Subsequently, 0.8 MPa of VDF was added followed by addition of TFE until the pressure reached 2.8 MPa. At this time, KMNO4 in a DI water solution (0.1 g/L) was injected at 80 mL/min until approximately 2 kg of TFE was added. After addition of the second Kg of TFE, the pressure in the reactor was reduced to 50 Kpa using vacuum and pressurized with fresh TFE to 2.8 MPa. The KMnO4 was added at 40 mL/min until the 4th Kg of TFE was consumed. After the 4th Kg of TFE was added, KMnO4 was no longer added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 42.76 Kg containing 29.0% solids. The dispersion was coagulated with Nitric acid and dried at 170° C.

The raw dispersion particle size (RDPS) of the polymer particle was 0.263 microns and the standard specific gravity was 2.157. The VDF concentration in the copolymer was measured to be 4.30 mol % (2.80 wt %). The PFBE concentration in the copolymer was measured to be 0.03 mol % (0.07 wt %), yielding a total copolymer concentration in the composition of 2.87 wt %. The break strength of the beading specimen was 13.6 lbs.

The matrix tensile strength of the specimen was measured to be 44,878 psi.

EXAMPLE 4

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

To the evacuated reactor, 19.94 g of PFOE was charged, and the reactor was heated to 83 C and agitated at 60 rpm. Subsequently, 0.8 MPa of VDF was added followed by addition of TFE until the pressure reached 2.8 MPa. At this time, KMNO4 in a DI water solution (0.1 g/L) was injected at 80 mL/min until approximately 2 kg of TFE was added. After addition of the second Kg of TFE, the pressure in the reactor was reduced to 50 Kpa using vacuum and pressurized with fresh TFE to 2.8 MPa. The KMnO4 was again added at 40 mL/min until an additional 0.5 Kg of TFE was consumed and reduced to 20 mL/min until 4 Kg of TFE was consumed. After the 4th Kg of TFE was added, KMnO4 was no longer added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 42.82 Kg containing 28.4% solids. The dispersion was coagulated with Nitric acid and dried at 170° C.

The raw dispersion particle size (RDPS) of the polymer particle was 0.240 microns and the standard specific gravity was 2.159. The VDF concentration in the copolymer was measured to be 3.50 mol % (2.20 wt %). The PFOE concentration in the copolymer was measured to be 0.03 mol % (0.16 wt %), yielding a total copolymer concentration in the composition of 2.36 wt %. The break strength of the beading specimen was 14.1 lbs.

The matrix tensile strength of the specimen was measured to be 48,236 psi.

EXAMPLE 5

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

To the evacuated reactor, 8 mL of PFBE were charged, and the reactor was heated to 83° C. and agitated at 60 rpm. Subsequently, TFE was added until the pressure reached 2.8 MPa. At this time, KMnO4 in a DI water solution (0.063 g/L) was injected at 80 mL/min until approximately 1 kg of TFE was added. At this time the pressure in the reactor was reduced to 50 Kpa using vacuum and pressurized with 0.8 MPa of VDF followed by addition of TFE until the pressure reached 2.8 MPa. The KMnO4 was again added at 80 mL/min until an additional 1 Kg of TFE was consumed at which time it was reduced to 40 mL/min until 4 Kg of TFE was consumed. After the fourth Kg of TFE was consumed the pressure in the reactor was reduced to 50 Kpa using vacuum and pressurized with fresh TFE to 2.8 MPa. An additional amount of KMnO4 was added at 10 mL/min until the fifth Kg of TFE was consumed. After the consumption of the fifth Kg of TFE, no more KMnO4 was added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 48.8 Kg containing 34.5% solids. The dispersion was coagulated with Nitric acid and dried at 170° C.

The raw dispersion particle size (RDPS) of the polymer particle was 0.234 microns and the standard specific gravity was 2.151. The VDF concentration in the copolymer was measured to be 3.15 mol % (2.04 wt %), and the PFBE concentration in the copolymer was measured to be 0.03 mol % (0.07 wt %), yielding a total copolymer concentration in the composition of 2.11 wt %. The break strength of the beading specimen was 8.6 lbs.

The matrix tensile strength of the specimen was 10 measured to be 31,342 psi.

EXAMPLE 6

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83° C. and agitated at 60 rpm. Subsequently, TFE was added until the pressure reached 2.8 MPa. At this time, KMnO4 in a DI water solution (0.063 g/L) was injected at 80 mL/min until approximately 1 kg of TFE was added. At this time the pressure in the reactor was reduced to 50 Kpa using vacuum and pressurized with 0.8 MPa of VDF followed by addition of TFE until the pressure reached 2.8 MPa. The KMnO4 was again added at 80 mL/min until an additional 2 Kg of TFE was consumed at which time it was reduced to 40 mL/min until 4 Kg of TFE was consumed. After the fourth Kg of TFE was consumed the pressure in the reactor was reduced to 50 Kpa using vacuum and pressurized with fresh TFE to 2.8 MPa. An additional amount of KMnO4 was added at 40 mL/min until the fifth Kg of TFE was consumed. After the consumption of the fifth Kg of TFE, no more KMnO4 was added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 46.86 Kg containing 35.0% solids. The dispersion was coagulated with Nitric acid and dried at 170° C.

The raw dispersion particle size (RDPS) of the polymer particle was 0.265 microns and the standard specific gravity was 2.158. The VDF concentration in the copolymer was measured to be 3.35 mol % (2.17 wt %). The break strength of the beading specimen was 6.6 lbs. An SEM of the microstructure of the beading specimen is shown in FIG. 2.

The matrix tensile strength of the specimen was measured to be 26,053 psi.

The copolymer material formed in this example was then blended with Isopar K (Exxon Mobil Corp., Fairfax, Va.) in the proportion of 0.196 g/g of fine powder. The lubricated powder was compressed into a cylinder to form a pellet and placed into an oven set at 49° C. for approximately 12 hours. The compressed and heated pellet was ram extruded to produce a tape approximately 16.0 cm wide by 0.73 mm thick. The extruded tape was then rolled down between compression rolls to a thickness of 0.256 mm. The tape was then transversely stretched to approximately 56 cm wide (i.e., at a ratio of 3.5:1) and dried at a temperature of 250° C. The dry tape was longitudinally expanded between banks of rolls over a heated plate set to a temperature of 345° C. The speed ratio between the second bank of rolls and the first bank of rolls was 10:1. The width of the expanded tape was 12.1 cm. The longitudinally expanded tape was then expanded transversely at a temperature of approximately 360° C. to a ratio of approximately 25:1 and then constrained from shrinkage and heated in an oven set at 380° C. for approximately 24 seconds. An SEM of the resulting sheet is shown in FIG. 3, taken at 20,000× magnification, showing a node 1 and fibril 2 microstructure.

EXAMPLE 7

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

To the evacuated reactor, 8 mL of PFBE was charged, and the reactor was heated to 83° C. and agitated at 60 rpm. Subsequently, TFE was added until the pressure reached 2.8 MPa. At this time, KMnO4 in a DI water solution (0.063 g/L) was injected at 80 mL/min until approximately 1 kg of TFE was added. At this time the pressure in the reactor was reduced to 50 Kpa using vacuum and pressurized with 0.8 MPa of TrFE followed by addition of TFE until the pressure reached 2.8 MPa. The KMnO4 was again added at 80 mL/min until an additional 3 Kg of TFE was consumed. After the fourth Kg of TFE was consumed the pressure in the reactor was reduced to 50 Kpa using vacuum and pressurized with fresh TFE to 2.8 MPa. An additional amount of KMnO4 was added at 40 mL/min until the fifth Kg of TFE was consumed. After the consumption of the fifth Kg of TFE, no more KMnO4 was added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 46.9 Kg containing 33.1% solids. The dispersion was coagulated with Nitric acid and dried at 170° C.

The raw dispersion particle size (RDPS) of the polymer particle was 0.227 microns and the standard specific gravity was 2.217. The TrFE concentration in the copolymer was measured to be 4.2 mol % (3.5 wt %), and the PFBE concentration in the copolymer was measured to be 0.03 mol % (0.07 wt %), yielding a total copolymer concentration in the composition of 3.57 wt %. The break strength of the beading specimen was 3.48 lbs.

The matrix tensile strength of the specimen was measured to be 13,382 psi.

EXAMPLE 8

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83° C. and agitated at 60 rpm. Subsequently, TFE was added until the pressure reached 2.8 MPa. At this time, KMnO4 in a DI water solution (0.063 g/L) was injected at 80 mL/min until approximately 1 kg of TFE was added. At this time the pressure in the reactor was reduced to 50 Kpa using vacuum and pressurized with 0.8 MPa of TrFE followed by addition of TFE until the pressure reached 2.8 MPa. The KMnO4 was again added at 80 mL/min until an additional 3 Kg of TFE was consumed. After the fourth Kg of TFE was consumed the pressure in the reactor was reduced to 50 Kpa using vacuum and pressurized with fresh TFE to 2.8 MPa. An additional amount of KMnO4 was added at 40 mL/min until the fifth Kg of TFE was consumed. After the consumption of the fifth Kg of TFE, no more KMnO4 was added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 4722 Kg containing 34.8% solids. The dispersion was coagulated with Nitric acid and dried at 170° C.

The raw dispersion particle size (RDPS) of the polymer particle was 0.276 microns and the standard specific gravity was 2.219. The TrFE concentration in the copolymer was measured to be 4.17 mol % (3.5 wt %). The break strength of the beading specimen was 3.95 lbs.

The matrix tensile strength of the specimen was measured to be 15,329 psi.

EXAMPLE 9

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83° C. and agitated at 6 0 rpm. Subsequently, TFE was added until the pressure reached 2.8 MPa. At this time, KMnO4 in a DI water solution (0.063 g/L) was injected at 80 mL/min until approximately 1 kg of TFE was added. At this time the pressure in the reactor was reduced to 50 Kpa using vacuum and pressurized with 1.2 Kg of HFP followed by addition of TFE until the pressure reached 1.9 MPa. The KMnO4 was again added at 80 mL/min until an additional three Kg of TFE was consumed. After the 4$^{th}$ Kg of TFE was consumed the pressure in the reactor was reduced to 50 Kpa using vacuum and pressurized with fresh TFE to 2.8 MPa. An additional amount of KMnO4 was added at 80 mL/min until the fifth Kg of TFE was consumed. After the consumption of the fifth Kg of TFE, no more KMnO4 was added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 48.54 Kg containing 30.4% solids. The dispersion was coagulated with Nitric acid and dried at 170° C.

The raw dispersion particle size (RDPS) of the polymer particle was 0.302 microns and the standard specific gravity was 2.157. The HFP concentration in the copolymer was measured to be 0.77 mol % (1.25 wt %). The break strength of the beading specimen was 7.60 lbs.

The matrix tensile strength of the specimen was measured to be 34,178 psi.

EXAMPLE 10

To a 50-liter, horizontal polymerization reactor equipped with a 3-bladed agitator was added 1.5 Kg wax, 28 Kg of deionized (DI) water, 18 g of ammonium perfluorooctanoic acid (APFO), 0.2 g FeSO4 and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83° C. and agitated at 60 rpm. Subsequently, 0.81 MPa of CTFE was added followed by addition of TFE until the pressure reached 2.8 MPa. At this time, a solution containing 3 g ammonium persulfate and 1 g sodium hydrosulfite in 2000 mL of DI water was injected at 40 mL/min until 2 Kg of TFE was consumed. After addition of the second Kg of TFE, the pressure in the reactor was reduced to 50 Kpa using vacuum and pressurized with fresh TFE to 2.8 MPa. Additional initiator solution was again added at 20 mL/Min until a total of 2.5 Kg of TFE was consumed. At this time the rate was reduced to 10 mL/min. After 3 Kg of total TFE was consumed no more initiator was added.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 16 Kg of TFE had been added to the reactor. The weight of the dispersion produced was 48.07 Kg containing 35.0% solids. The dispersion was coagulated with Nitric acid and dried at 170° C.

The raw dispersion particle size (RDPS) of the polymer particle was 0.245 microns and the standard specific gravity was 2.228. The CTFE concentration in the copolymer was measured to be 3.9 mol % (4.5 wt %). The break strength of the beading specimen was 7.6 lbs.

The matrix tensile strength of the specimen was measured to be 23,991 psi.

Figure 4:
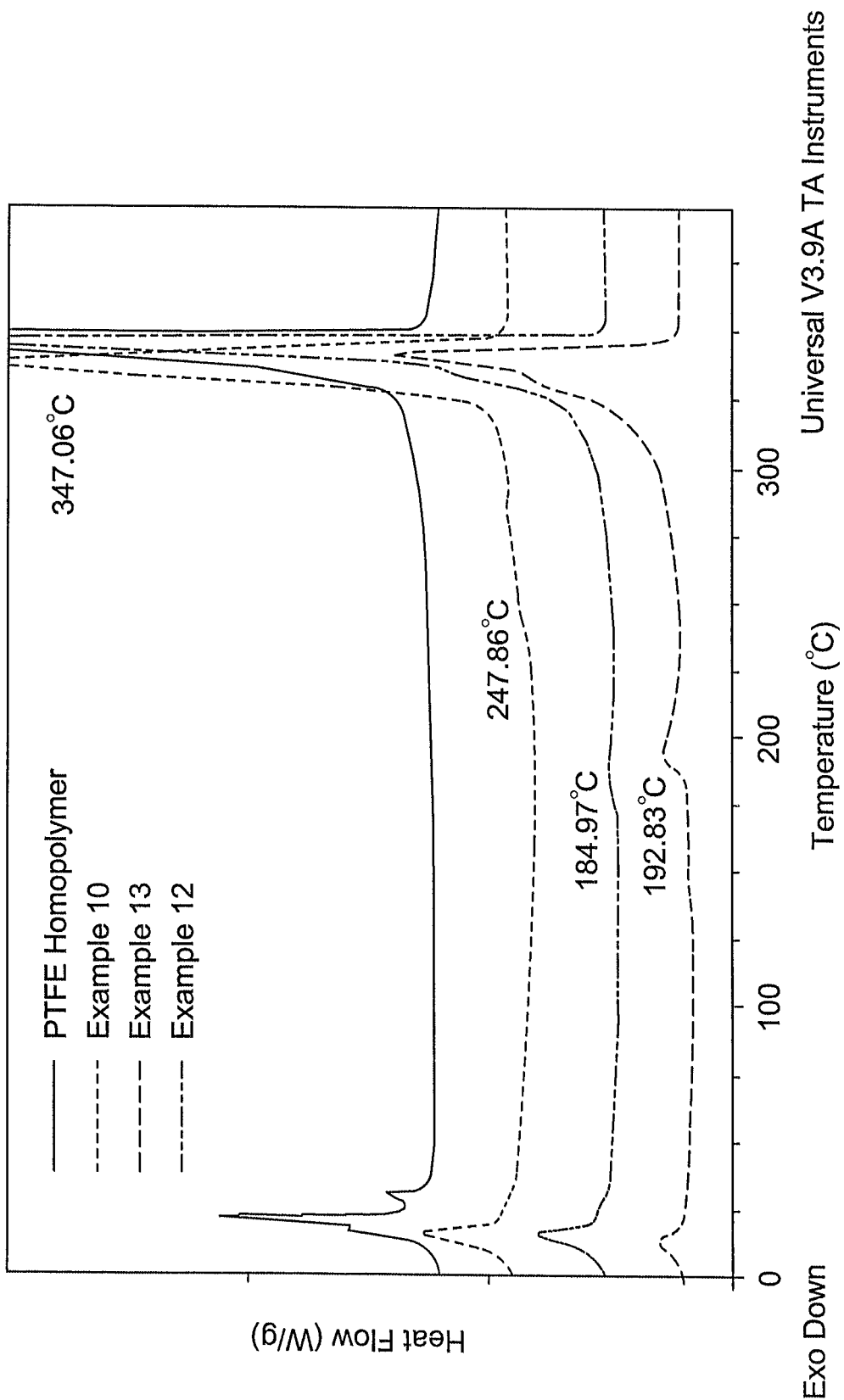
FIG. 4 includes differential scanning calorimetry (DSC) scans showing the melt transition temperature peaks of the materials of Examples 10, 12 and 13, as well as that of a comparative PTFE homopolymer.

Adhesion testing was performed, and the results are reported in Table 2. A DSC scan for this material is included in FIG. 4, which shows a first melt transition for the material at about 247° C.

EXAMPLE 11

To a 50-liter, horizontal polymerization reactor equipped with a 3-bladed agitator was added 1.5 Kg wax, 28 Kg of deionized (DI) water, 18 g of ammonium perfluorooctanoic acid (APFO), 0.2 g FeSO4 and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

To the evacuated reactor, 8 mL of PFBE was charged, and the reactor was heated to 83N C. and agitated at 60 rpm. Subsequently, 0.81 MPa of CTFE was added followed by addition of TFE until the pressure reached 2.8 MPa. A solution containing 3 g ammonium persulfate and 1 g sodium hydrosulfite in 2000 mL of DI water was injected at 40 mL/min until 2 Kg of TFE were consumed. After addition of the second Kg of TFE, the pressure in the reactor was reduced to 50 KPa using vacuum and pressurized with fresh TFE to 2.8 MPa. Additional initiator solution was again added at 20 mL/Min until a total of 3.0 Kg of TFE was consumed. After the third Kg of TFE was consumed, no more initiator was added.

Approximately 320 g of 20% APFO solution was added in 40 mL increments, the first increment being added after about 1 Kg of TFE had been added, followed by increments after each additional Kg of TFE, so that the final increment was added after 8 kg of TFE had been reacted.

The polymerization reaction was then allowed to continue and the reaction stopped after 16 Kg of TFE had been added to the reactor. The weight of the dispersion produced was 47.19 Kg containing 36.6% solids. The dispersion was coagulated with Nitric acid and dried at 170° C.

The raw dispersion particle size (RDPS) of the polymer particle was 0.178 microns and the standard specific gravity was 2.247. The CTFE concentration in the copolymer was measured to be 3.1 mol % (3.70 wt %) and the PFBE concentration in the polymer was measured to be 0.03 mol % (0.07 wt %), yielding a total copolymer concentration in the composition of 3.77 wt %.

The break strength of the beading specimen was 3.48 lbs.

EXAMPLE 12

To a 50-liter, horizontal polymerization reactor equipped with a 3-bladed agitator was added 1.5 Kg wax, 28 Kg of deionized (DI) water, 18 g of ammonium perfluorooctanoic acid (APFO) and 5 g of succinic acid dissolved in about 50 g of DI water. The reactor and contents were heated above the melting point of the wax.

The reactor was repeatedly evacuated and pressurized (to about 1 Atm or less) with TFE until the oxygen level was reduced to 20 ppm or less. The contents were briefly agitated at about 60 rpm between evacuation and purge cycles to ensure that the water was deoxygenated.

The reactor was heated to 83° C., and agitated at 60 rpm. Subsequently, 2.0 MPa of VDF was added followed by addition of TFE until the pressure reached 2.8 MPa. At this time, KMnO4 in a DI water solution (0.063 g/L) was injected at 80 mL/min until approximately 4 kg of TFE were added. The KMnO4 was added at 40 mL/min during addition of the next 2 kg of TFE. After 6 Kg of TFE was consumed, no more KMnO4 was added.

Approximately 320 g of 20% APFO solution were added in 40 mL increments, the first increment being added after about 1 kg of TFE had been added, followed by increments after each additional Kg of TFE, so that the final increment was added after 8 kg of TFE had been reacted.

The polymerization reaction was then allowed to continue and the reaction stopped after 16 Kg of TFE had been added to the reactor. The weight of the dispersion produced was 48.64 Kg containing 31.2% solids. The dispersion was coagulated with Nitric acid and dried at 170° C.

The raw dispersion particle size (RDPS) of the polymer particle was 0.321 microns and the standard specific gravity was 2.137. The VDF concentration in the copolymer was measured to be 11.8 mol % (7.90 wt %).

The break strength of the beading specimen was 10.53 lbs. The matrix tensile strength of the specimen was measured to be 37,000 psi.

Adhesion testing was performed, and the results are reported in Table 2. A DSC scan for this material is included in FIG. 4, which shows a first melt transition for the material at about 185° C.

EXAMPLE 13

To a 50-liter, horizontal polymerization reactor equipped with a 3-bladed agitator was added 1.5 Kg wax, 28 Kg of deionized (DI) water, 18 g of ammonium perfluorooctanoic acid (APFO), 1.5 g of $ZnCl_2$, and 5 g of succinic acid dissolved in about 50 g of DI water. The reactor and contents were heated above the melting point of the wax. The reactor was repeatedly evacuated and pressurized (to about 1 Atm or less) with TFE until the oxygen level was reduced b 20 ppm or less. The contents were briefly agitated at about 60 rpm between evacuation and purge cycles to ensure that the water was deoxygenated.

The reactor was heated to 83° C. and agitated at 60 rpm. Subsequently, 2.0 MPa of VDF was added followed by addition of TFE until the pressure reached 2.8 MPa. At this time, $KMnO_4$ in a DI water solution (0.1 g/L) was injected at 80 mL/min until was approximately 4 kg of TFE were added. The $KMnO_4$ was added at 40 mL/min during the next 2 Kg TFE addition. After 5 Kg of TFE was consumed an additional 1 g of initiator solution was added. The total amount of $KMnO_4$ solution added was 3.375 Kg.

Approximately 320 g of 20% APFO solution was added in 40 mL increments, the first increment being added after about 1 Kg of TFE had been added, followed by increments after each additional Kg of TFE, so that the final increment was added after 8 Kg of TFE had been reacted.

The polymerization reaction was then allowed to continue and the reaction stopped after 9 Kg of TFE had been added to the reactor. The weight of the dispersion produced was 40.18 Kg containing 19.6% solids. The dispersion was coagulated with Nitric acid and dried at 170° C. The raw dispersion particle size (RDPS) of the polymer particle was 0.339 microns. The VDF concentration in the copolymer was measured to be 23.8 mol % (16.7 wt %). The Break strength of the beading specimen was 8.62 lbs. The matrix tensile strength of the specimen was measured to be 23,511 psi.

Adhesion testing was performed, and the results are reported in Table 2. A DSC scan for this material is included in FIG. 4, which shows a first melt transition for the material at about 193° C.

A summary of the results given in the above Examples is provided in Table 1. Adhesion results are reported in Table 2. The foregoing examples are provided to illustrate, without limitation, certain preferred embodiments of copolymers produced according to the principles described herein. Additional copolymers, terpolymers, etc., incorporating comonomers that are known to be reactive with TFE, can also be used. These additional comonomers can be added in a predetermined concentration and allowed to react, with or without evacuation, based on the monomers' reactivity ratio to TFE, all of which is known to one skilled in the art, as illustrated in the published literature (see, e.g., *Well-Architectured Fluoropolymers: Synthesis, Properties, and Applications*; Elsevier; Amsterdam 2004, pp. 209).

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

TABLE 1

| Example | Added comonomer(s) | Particle size, microns | SSG | Extrusion pressure, psig | Extrudate strength, psi | Break strength, lbs | MTS, psi |
|---|---|---|---|---|---|---|---|
| 1 | VDF | 0.296 | 2.156 | 3500 | 1046 | 10.40 | 37,299 |
| 2 | TrFE | 0.283 | 2.213 | 3501 | 926 | 7.24 | 28,602 |
| 3 | VDF/PFBE | 0.263 | 2.157 | 3956 | 1139 | 13.60 | 44,878 |
| 4 | VDF/PFOE | 0.240 | 2.159 | 4294 | 1257 | 14.10 | 48,236 |
| 5 | VDF/PFBE | 0.234 | 2.151 | 3434 | 944 | 8.60 | 31,342 |
| 6 | VDF | 0.265 | 2.158 | 3123 | 862 | 6.60 | 26,053 |
| 7 | TrFE/PFBE | 0.227 | 2.217 | 3522 | 963 | 3.48 | 13,382 |
| 8 | TrFE | 0.276 | 2.219 | 3085 | 847 | 3.95 | 15,329 |
| 9 | HFP | 0.300 | 2.157 | 3350 | 988 | 7.60 | 34,178 |
| 10 | CTFE | 0.245 | 2.228 | 3640 | 953 | 7.60 | 23,991 |
| 11 | CTFE/PFBE | 0.177 | 2.247 | 3817 | 1071 | 5.50 | 15,722 |
| 12 | VDF | 0.321 | 2.137 | 4110 | 1044 | 10.53 | 37,000 |
| 13 | VDF | 0.339 | n/a | 5680 | 1061 | 8.62 | 23,511 |

TABLE 2

| Materials | Adhesion measure at 195° C. (J/m²) | Adhesion measure at 290° C. (J/m²) | Adhesion measure at 350° C. (J/m²) |
|---|---|---|---|
| PTFE Homopolymer | No Adhesion | No Adhesion | 69.2 |
| Example 10 | No Adhesion | 88.5 | 89.2 |
| Example 12 | 87.2 | 221 | 521 |
| Example 13 | 15.3 | 105.3 | 383.5 |

What is claimed is:

1. An expandable tetrafluoroethylene (TFE) copolymer comprising:
    (a) a first, core portion comprising a polymer chain of TFE monomers and at least one other comonomer comprising a perfluoroalkyl vinyl ether monomer; and
    (b) a second, shell portion consisting of a polymer chain consisting of TFE monomers,
    wherein said expandable core-shell tetrafluoroethylene copolymer comprises at least 3.0% by weight polymerized units of said at least one other comonomer based on total weight of said copolymer, and
    wherein said copolymer exhibits adhesion after subjecting the copolymer to a temperature at or below about 290° C.

2. The copolymer of claim 1, wherein said perfluoroalkyl vinyl ether monomer is PMVE.

3. The copolymer of claim 1, wherein said perfluoroalkyl vinyl ether monomer is PEVE.

4. The copolymer of claim 1, wherein said perfluoroalkyl vinyl ether monomer is PPVE.

5. The copolymer of claim 1, including more than one other comonomer.

6. The copolymer of claim 1, having at least 5.0% by weight polymerized units of at least one other comonomer based on total weight of said copolymer.

7. The copolymer of claim 1, in the form of fine particles dispersed within an aqueous medium.

8. The copolymer of claim 1, in the form of fine powder.

9. The copolymer of claim 1, wherein said copolymer comprises a first melt transition temperature and a second melt transition temperature.

10. The copolymer of claim 1, wherein said copolymer exhibits adhesion.

11. An expandable tetrafluoroethylene (TFE) copolymer comprising:
    (a) a first, core portion comprising a polymer chain of TFE monomers and at least one other comonomer comprising a perfluoroalkyl vinyl ether monomer; and
    (b) a second, shell portion consisting of a polymer chain consisting of TFE monomers,
    wherein said expandable core-shell tetrafluoroethylene copolymer comprises at least 3.0% by weight polymerized units of said at least one other comonomer based on total weight of said copolymer,
    wherein said copolymer exhibits adhesion after subjecting the copolymer to its first melt transition temperature or above.

12. The copolymer of claim 11, wherein said perfluoroalkyl vinyl ether monomer is PMVE.

13. The copolymer of claim 11, wherein said perfluoroalkyl vinyl ether monomer is PEVE.

14. The copolymer of claim 11, wherein said perfluoroalkyl vinyl ether monomer is PPVE.

15. The copolymer of claim 11, including more than one other comonomer.

16. The copolymer of claim 11, having at least 5.0% by weight polymerized units of at least one other comonomer based on total weight of said copolymer.

17. The copolymer of claim 11, in the form of fine particles dispersed within an aqueous medium.

18. The copolymer of claim 11, in the form of fine powder.

19. An expandable tetrafluoroethylene (TFE) copolymer comprising:
    (a) a first, core portion comprising a polymer chain of TFE monomers and at least one other comonomer comprising a perfluoroalkyl vinyl ether monomer; and
    (b) a second, shell portion consisting of a polymer chain consisting of TFE monomers,
    wherein said expandable core-shell tetrafluoroethylene copolymer comprises at least 3.0% by weight polymerized units of said at least one other comonomer based on total weight of said copolymer,
    wherein said copolymer exhibits adhesion after subjecting the copolymer to a temperature between its first melt transition temperature and about 290° C.

20. The copolymer of claim 19, wherein said perfluoroalkyl vinyl ether monomer is PMVE.

21. The copolymer of claim 19, wherein said perfluoroalkyl vinyl ether monomer is PEVE.

22. The copolymer of claim 19, wherein said perfluoroalkyl vinyl ether monomer is PPVE.

23. The copolymer of claim 19, including more than one other comonomer.

24. The copolymer of claim 19, having at least 5.0% by weight polymerized units of at least one other comonomer based on total weight of said copolymer.

25. The copolymer of claim 19, in the form of fine particles dispersed within an aqueous medium.

26. The copolymer of claim 19, in the form of fine powder.

* * * * *